US007829072B2

(12) United States Patent
Carter

(10) Patent No.: US 7,829,072 B2
(45) Date of Patent: Nov. 9, 2010

(54) SERUM ALBUMIN COMPOSITIONS FOR USE IN CLEANSING OR DERMATOLOGICAL PRODUCTS FOR SKIN OR HAIR

(76) Inventor: Daniel C. Carter, 119 Wood Creek Dr., Madison, AL (US) 35758

( * ) Notice: Subject to any disclaimer, the term of this patent is extended or adjusted under 35 U.S.C. 154(b) by 0 days.

(21) Appl. No.: 09/740,821

(22) Filed: Dec. 21, 2000

(65) Prior Publication Data

US 2002/0006892 A1    Jan. 17, 2002

Related U.S. Application Data

(63) Continuation-in-part of application No. 09/616,962, filed on Jul. 14, 2000.

(51) Int. Cl.
*A61K 38/38* (2006.01)
*A61K 8/18* (2006.01)
*A61K 38/00* (2006.01)

(52) U.S. Cl. .................. 424/70.19; 424/401; 514/881; 530/363

(58) Field of Classification Search .............. 514/2; 430/362, 363, 364; 435/440, 69.1, 320.1, 435/350; 424/401; 530/350
See application file for complete search history.

(56) References Cited

U.S. PATENT DOCUMENTS

| | | | | | |
|---|---|---|---|---|---|
| 4,942,179 | A | * | 7/1990 | Borgarello et al. | 514/659 |
| 5,254,331 | A | * | 10/1993 | Mausner | 424/59 |
| 5,545,722 | A | * | 8/1996 | Naka | 530/399 |
| 5,641,483 | A | * | 6/1997 | Beaulieu | 424/78.06 |
| 5,693,318 | A | * | 12/1997 | Burke et al. | 424/78.02 |
| 5,759,802 | A | * | 6/1998 | Maki et al. | 435/69.1 |
| 5,997,904 | A | * | 12/1999 | Magdassi et al. | 424/489 |
| 6,036,966 | A | | 3/2000 | Youssefyeh | |
| 6,488,928 | B1 | * | 12/2002 | Maurin et al. | 424/94.6 |
| 6,787,636 | B1 | * | 9/2004 | Carter | 530/363 |

FOREIGN PATENT DOCUMENTS

| | | | |
|---|---|---|---|
| EP | 0180968 | * | 5/1985 |
| EP | 0 180 968 | | 5/1986 |
| EP | 180968 A | * | 5/1986 |
| EP | 0 244 859 | | 11/1987 |
| EP | 0244859 | * | 11/1987 |
| WO | WO 00/20454 | | 4/2000 |
| WO | WO-01/91713 | | 12/2001 |
| WO | WO-02/05645 | | 1/2002 |
| WO | WO 02/49671 | | 6/2002 |

OTHER PUBLICATIONS

Petersen, C. E. et al (1997)"Mutagenesis studies of tyroxine binding to human serum albumin define an important structural characteristics of subdomain 2A", Biochemistry vol. 36, 7012-7017).*
Ngo, J. T. et al. et al. (1994) "Computational complexity protein structure prediction, and the levinthal paradox". In "The protein folding problem and tertiary structure prediction". pp. 491-495, Merz, Jr. K. et al. Eds. Birkhauser, Boston.*
Kragh-Hansen, U. et al. (1994) Modified high-affinity binding of Ni2+, Ca2+ and Zn2+ to natural mutants of human serum albumin and proalbumin. Biochem. J. vol. 301 ( Pt 1), pp. 217-223.*
Palma et al. (2002) Evaluation of the surfactant properties of ascorbyl palmitate sodium salt. Eur. J. Pharm. Sci. vol. 16, No. 1-2, pp. 37-43.*
Kiwi Web (2005) Synthetic detergent, http://www.chemistry.co.nz/introduction.htm, p. 1.*
Carol, B. (1995) The harzards of Cosmetics, pp. 1-5 (sorted out by http://www.envronmentalhealth.ca/summer95cosmetic.html.*
Nielsen et al. (Jun. 2000) Thermochemistry of the specific binding of C12 surfactants to bovine serum albumin. Biochim. Biophys. Acta. vol. 1479, Nos. 1-2, pp. 321-331.*
Paula Begoun—the cosmetics cop. (2005) Cosmetic ingredient dictionary, "sodium laureth sulfate" section, pp. 1-2.*
Eppler et al. (2004) Assessment of Skin Absorption and Metabolism of. Arachidonic Acid & Glyceryl Arachidonate Using in Vitro. Diffusion Cell Techniques, Mattek Corporation, refrence 338, p. 1.*
Tree of Life Product (2007, updated) http://www.tarahill.com/treeolif/ingred.html, pp. 1-2.*
Flexall Product Support (2007, updated) http://www.ari-med.com/flexall_product_support.php, pp. 1-3.*
Tarelli et al. (1998) Recombinant human albumin as a stabilizer for biological materials and for the preparation of international reference reagents. Biologicals. vol. 26, No. 4, pp. 331-346.*
Net Wellness (2007, updated) Common Ingredients in Skin Care Products, http://www.netwellness.org/healthtopics/skincare/faq4.cfm, pp. 1-7.*
Dictionary (2007, updated) "Soap", http://www.thefreedictionary.com/soap, p. 1.*

(Continued)

*Primary Examiner*—Anand U Desai
*Assistant Examiner*—Samuel Liu
(74) *Attorney, Agent, or Firm*—B. Aaron Schulman; Stites & Harbison PLLC

(57) ABSTRACT

A hypoallergenic cleansing, cosmetic, conditioning or dermatological composition for treating skin or hair is provided which contains serum albumin in an amount effective to achieve cleansing, conditioning, wound debrisment, or other beneficial cosmetic or dermatological purpose for skin or hair, along with a suitable cleansing, conditioning, cosmetic, antibacterial or dermatological agent, vehicle, carrier or excipient. The compositions may be in any suitable form for treating skin or hair, such as a soap, shampoo, cream, oil, lotion, gel, gel-based ointment, and the like. The serum albumin compositions are preferably prepared using human serum albumin produced by recombinant means, and such compositions are useful in that they allow the albumin to be absorbed in the surface of skin or hair so as to replenish the structure of these tissues when utilized as a cleansing, cosmetic or dermatological agent. The compositions of the present invention will provide cleansing, cosmetic or dermatological compositions that can be used safely and effectively with reduced likelihood of allergic reaction.

3 Claims, No Drawings

OTHER PUBLICATIONS

Cosmetics Info (2007, updated) Steareth-21, http://www.cosmeticsinfo.org/ingredient_details.php?ingredient_id=1650, pp. 1-2.*

Chan et al., "Site-specific N-terminal auto-degradation of human serum albumin", European Journal of Biochemistry, vol. 227, No. 1-2, 1995, pp. 524-528.

Sadler et al., Involvement of a lysine residue in the N-terminal Ni2+ and Cu2+ binding site of serum albumins, European Journal of Biochemistry, vol. 220, No. 1, 1994, pp. 193-200.

Takahashi, Nobuhiro, Structural changes and metal binding by proalbumins and other amino-terminal genetic variants of human serum albumin; Jun. 22, 1987, 7403-7407, vol. 84, Nov. 1987, Proceedings of the National Academy of Sciences of USA, National Academy of Science, Washington, US.

Bar-Or, D. et al, Characterization of the CO2+ and NI2+ Binding Amino-Acid Residues of the N-Terminus of Human Albumin an Insight Into the Mechanism of a New Assay for Myocardial Ischemia, Jan. 2001, pp. 42-47, vol. 268, No. 1, European Journal of Biochemistry, Berlin, DE.

Database WPI, Section Ch, Week 199527, Derwent Publications Ltd., London, GB, AN 1995-200996 & CN 1 085 424 (Shan K) Apr. 20, 1994 *abstract*.

* cited by examiner

SERUM ALBUMIN COMPOSITIONS FOR USE IN CLEANSING OR DERMATOLOGICAL PRODUCTS FOR SKIN OR HAIR

This application is a continuation-in-part of co-pending U.S. application Ser. No. 09/616,962, filed Jul. 14, 2000.

FIELD OF THE INVENTION

This invention relates in general to the use of a serum albumin composition as a cleansing or dermatological agent, and more specifically relates to the use of serum albumin, preferably human serum albumin produced by recombinant means, in shampoos, soaps, creams and oils for cleansing or dermatological use which will allow the albumin to be absorbed in the surface of skin or hair and replenish its structure as a natural component and which can be used safely and effectively with reduced likelihood of allergic reaction.

BACKGROUND OF THE INVENTION

The serum albumins belong to a multigene family of proteins that includes alpha-fetoprotein and human group-specific component, also known as vitamin-D binding protein. The members of this multigene family are typically comprised of relatively large multi-domain proteins, and the serum albumins are the major soluble proteins of the circulatory system and contribute to many vital physiological processes. Serum albumin generally comprises about 50% of the total blood component by dry weight, and as such is responsible for roughly 80% of the maintenance of colloid osmotic blood pressure and is chiefly responsible for controlling the physiological pH of blood.

The albumins and their related blood proteins also play an extremely important role in the transport, distribution and metabolism of many endogenous and exogenous ligands in the human body, including a variety of chemically diverse molecules including fatty acids, amino acids, steroids, calcium, metals such as copper and zinc, and various pharmaceutical agents. The albumin family of molecules are generally thought to facilitate transfer many of these ligands across organ-circulatory interfaces such as the liver, intestines, kidneys and the brain, and studies have suggested the existence of an albumin cell surface receptor. See, e.g., Schnitzer et al., *P.N.A.S.* 85:6773 (1988). The albumins are thus involved in a wide range of circulatory and metabolic functions.

Human serum albumin (HSA) is a protein of about 66,500 kD protein and is comprised of 585 amino acids including at least 17 disulphide bridges. As with many of the members of the albumin family, human serum albumin plays an extremely important role in human physiology and is located in virtually every human tissue and bodily secretion. In fact, human serum albumin appears to be the largest single natural protein component of skin, and approximately 40% of extravascular albumin is located in the skin. Further, as indicated above, HSA has an outstanding ability to bind and transport a wide spectrum of ligands throughout the circulatory system including the long-chain fatty acids which are otherwise insoluble in circulating plasma. The atomic structure and particular details regarding the binding affinities of albumin and the specific regions primarily responsible for those binding properties have been previously determined as set forth, e.g., in U.S. Ser. No. 08/448,196, filed May 25, 1993, now U.S. Pat. No. 5,780,594 and U.S. Ser. No. 08/984,176, filed Dec. 3, 1997, now U.S. Pat. No. 5,948,609, both of which are incorporated herein by reference.

In the field of moisturizing and conditioning products for use on human skin and hair, although there have been hair conditioning products which use hydrolyzed proteins as active components, there has been no prior use of human albumin, specifically recombinant human albumin, as an active component of soaps for use as shampoos and in hand and body cleansing. Moreover, the use of hydrolyzed proteins has not significantly increased the effectiveness of the cleansing and conditioning products containing such hydrolyzed proteins because these proteins are grossly denatured and do not represent replacement of natural non-denatured and specific proteins of interest in skin and hair. Even further, other prior art products have focused on moisturizers and other similar products which utilize urea or lanolin based additives which once again do not provide adequate replacement of the natural non-denatured serum albumin proteins in skin.

There is thus a significant need to develop safe and effective cleansing and conditioning products which can provide absorbable non-denatured serum albumin to replace the natural protein and thus improve conditioning and treatment of hair and skin, and yet which can be used safely and effectively with a reduced risk of allergic reactions.

SUMMARY OF THE INVENTION

Accordingly, it is thus an object of the present invention to provide a novel skin and hair treating composition which utilizes human serum albumin, and more specifically which comprises recombinant human serum albumin.

It is further an object of the present invention to utilize recombinant human serum albumin as a cleansing, cosmetic or dermatological agent for human skin and hair which can replace natural albumin protein in the tissues in a safe and effective manner.

It is still further an object of the present invention to provide a composition for use in cleansing, conditioning and moisturizing skin or hair which can be used safely and effectively with a reduced risk of causing an allergic reaction.

It is even further an object of the present invention to provide albumin compositions which can be used as soaps, shampoos, creams, oils, lotions, gels or gel-based ointments, or any other form that is suitable for administration to skin or hair.

It is another object of the invention to provide suitable albumin-based compositions which can be used in solutions, creams, gels, ointments and the like for application to skin wounds so as to soothe the skin and promote healing, and to enhance wound debrisment.

These and other objects are achieved by virtue of the present invention which provides a hypoallergenic cleansing, cosmetic, conditioning or dermatological composition for treating skin or hair which comprises serum albumin in an amount effective to achieve cleansing, conditioning, or other beneficial cosmetic or dermatological purpose for skin or hair, along with a suitable cleansing, conditioning, cosmetic or dermatological agent, vehicle, carrier or excipient. The hypoallergenic albumin compositions of the invention may be in any suitable form for treating skin or hair, such as a soap, shampoo, cream, oil, lotion, gel, gel-based ointment, and the like. The serum albumin compositions are preferably prepared using recombinant serum albumin and are useful in that they allow the albumin to be absorbed in the surface of skin or hair so as to replenish its structure of these tissues when utilized as a cleansing, cosmetic or dermatological agent. The compositions of the present invention will provide cleansing, cosmetic or dermatological compositions that can be used safely and effectively with reduced likelihood of allergic reaction.

These and other features of the present invention as set forth in, or will become obvious from, the detailed description of the preferred embodiments provided hereinbelow.

DETAILED DESCRIPTION OF THE PREFERRED EMBODIMENTS

In accordance with the present invention, a skin and hair treating composition is provided which comprises serum albumin in an amount effective to achieve or enhance cleansing, conditioning, or other beneficial cosmetic or dermatological purpose for skin or hair, along with a suitable cleansing, conditioning, cosmetic or dermatological agent, vehicle, carrier or excipient. By effective amount is meant the amount of serum albumin used in the composition which will achieve or enhance a beneficial cosmetic or dermatological effect for skin or hair, such as cleansing, conditioning, moisturizing, etc., as would be readily understood by one skilled in the art. Accordingly, the actual amount of albumin used in the skin and hair treating compositions in the present invention will vary greatly depending on the type of albumin used, the desired effect, and the type of cosmetic or dermatological agent, vehicle, carrier, excipient, or other suitable cleansing or conditioning material used in the composition.

For example, in preparing compositions using a liquid soap base as the carrier, concentrations of albumin preferably range from 1 mg/ml to 60 mg/ml of the liquid soap base. However, depending on the specific purpose of the compositions or solutions of the invention, e.g., skin moisturizing, hair conditioning, shaving lotion, the amount of albumin used may vary, and can be adjusted based on the desired strength of the composition or solution. Accordingly, compositions in accordance with the invention can be prepared using albumin in concentrations as low as about 0.01 mg/ml or as high as about 250 mg/ml, which will again depend on the desired application and the nature of the carrier or base into which the albumin will be incorporated.

In another embodiment of the invention, a skin-treating composition can be prepared by incorporating an effective amount of albumin in a base of a material commonly used in cleansing or skin treating compositions, e.g., glycerin. In a preferred embodiment, a 10-60% glycerin solution, preferably about 15%, containing about 1-60 mg/ml of recombinant serum albumin, preferably about 40 mg/ml, can be prepared and employed as a treatment for chapped hands by application directly to the skin. The composition of the invention if useful in providing substantial softening and alleviation of chapped hands and other minor skin disorders.

In the preferred embodiment, the compositions of the present invention can be prepared by direct addition of the albumin to the cosmetic or dermatological agent or carrier, such as a liquid soap base, and the albumin may be added in any appropriate form, e.g., solid, freeze-dried, etc. With regard to the form of albumin useful in the compositions of the present invention, it is particularly preferred that human serum albumin be employed in these compositions, and preferably a recombinant serum albumin is used, such as those previously disclosed in U.S. Pat. Nos. 5,780,594 and 5,948,609, both of which are incorporated herein by reference. The albumin used may be in whole form or may be in the form of relevant fragments, such as particular domains, subdomains, etc., including those that have been disclosed in the patents referred to above. In addition, a modified or truncated human albumin such as disclosed in co-pending U.S. patent application Ser. No. 09/616,962, incorporated herein by reference, my also be utilized in the invention. As set forth in the co-pending application, the serum albumin may be one that has at least a one-amino acid truncation at its n-terminal end, or any other mutation at the n-terminal end which is sufficient to cause steric hindrance at the n-terminal end so as to reduce or eliminate the albumin's affinity to trace metals. Still other forms of albumin may also be suitable for certain applications.

As indicated above, the skin and hair treating albumin compositions of the present invention may take on a variety of forms which may be suitable for use as a cosmetic or dermatological agent. Such embodiments would include soaps, both liquid and dry forms, shampoos, oils, moisturizing cream, skin cosmetics, hand lotions, shaving creams, gels, gel-based ointments or any other application where the goal is treatment or conditioning of skin or hair. These forms are all well known in the art, as is well known the many conventional methods of preparing these cosmetic and dermatological forms which could be utilized to prepare the cosmetic, conditioning or dermatological compositions in accordance with the invention which contain an effective amount of serum albumin, preferably in recombinant form. Again, all of these cleansing and/or cosmetic forms in accordance with the invention will be comprised of an effective amount of albumin in a suitable base, i.e., an amount effective to achieve a desired cosmetic, cleansing, conditioning or dermatological purpose, as would be appropriate for the desired cosmetic, cleansing conditioning or dermatological application.

In addition, in accordance with the present invention, the albumin compositions of the present invention may also be utilized to promote soothing and healing of damaged skin or skin wounds, and thus may be used in sterile form as an emollient for treating such conditions. Similarly, the compositions of the invention may be used to promote the reduction or softening of scar tissue or for general wound debrisment, and in these cases it is desirable that the composition be made sterile in any conventional manner known in the art. One suitable possibility would be the preparation of sterile solutions in the form of gauze pads or other medical applicating forms that can be sealed to ensure sterility, and opened only at the time of use. Other suitable ingredients, such as physiologically acceptable anti-bacterial ingredients, may also be added to the sterile compositions as would be suitable for a desired application to skin.

The advantages of the present invention are exemplified in that conditioning, cleansing, skin softening, wound healing or debrisment, etc. using these albumin compositions and formulations will be enhanced and superior to formulations which do not include albumin because the compositions of the invention will allow for superior treatment of skin and hair using the largest single natural extracellular protein component, namely serum albumin. In addition, these compositions are highly desirable because serum albumin, particularly human serum albumin, may be produced recombinantly so as to be extremely safe in that it is non-blood derived and thus free of animal-derived pathogens. The preferred compositions of the present invention will also be hypoallergenic so as to reduce or eliminate the possibility of causing an allergic reaction upon application of the compositions.

The compositions of the present invention can thus be made simply and inexpensively using conventional ingredients and methods currently used in the conventional preparation of cosmetic or dermatological products such as soaps, shampoos, conditioners, moisturizers, etc. As indicated above, in the desired process, the albumin may be added directly to the cosmetic or dermatological base, such as by dissolving the serum albumin in a liquid soap base when it is desired to prepare a soap composition in accordance with the invention. However, as would be well known to those skilled in this art, there are numerous conventional processes that may be used to prepare the desired cosmetological or dermatological agent, and any suitable variety of these techniques may be employed to prepare the desired compositions in accordance with the invention.

Similarly, the present compositions will be useful in a variety of cosmetological and dermatological purposes, including as a cleanser, skin moisturizer, shampoo, shaving cream, etc., and the use of these forms of the invention will be by topical application in the conventional manner for the use of these products. The products obtained using the albumin compositions of the present invention will be superior to conventional conditioning, cleansing or moisturizing products in that they will have an enhanced cleansing, conditioning or moisturizing effect due to the use of the albumin. For example, shampoo formulations using the compositions of the present invention appears to reduce itching of the scalp and may prevent or reduce dandruff as well. In addition, the compositions of the invention provide effective skin softening and moisturizing products, and can be utilized as shampoos and conditioning agents which help add body and make hair more manageable.

Accordingly, the compositions of the present invention can be used to create a wide variety safe and effective cosmetic and dermatological products which have superior qualities when used as skin and hair treating agents. In addition, the compositions will be hypoallergenic and thus will reduce or eliminate the likelihood of causing an allergic reaction when used.

It is thus submitted that the foregoing embodiments are only illustrative of the claimed invention and not limiting of the invention in any way, and alternative embodiments that would be obvious to one skilled in the art not specifically set forth above also fall within the scope of the claims.

In addition, the following examples are presented as illustrative of the claimed invention, and are not deemed to be limiting of the scope of the invention, as defined by the claims appended hereto, in any manner.

EXAMPLES

Example 1

Compositions in accordance with the present invention were prepared by dissolving various concentrations of recombinant human serum albumin in an inexpensive conventional liquid soap base. These compositions were prepared by the direct addition of from 1 mg/ml to 60 mg/ml of recombinant human albumin in freeze-dried form to a liquid soap base, and the albumin dissolved immediately in the soap. The lower concentrations produced an interesting gelling effect on the soap which may also be desirable in product formation.

Example 2

Experimental use of the compositions of the present invention was made with five individuals who used the soap of Example 1 to wash their hands. All of the participants noted an immediate and distinctive difference in the texture and softness of the skin after drying their hands. In addition, preparations of the liquid composition were taken home by four individuals for trials to examine the conditioning properties when used as a shampoo or conditioner. All individuals noted a unique conditioning effect on the hair as well as a moisturizing effect on the skin. It appeared that the formulation of the invention reduced itching of the scalp and prevented dandruff formation as well.

The composition of the invention was thus used as a soap, a shampoo and a skin softener, and all were observed to have enhanced properties of softening, cleansing and/or conditioning.

Example 3

A composition in accordance with the present invention was prepared using a 15% glycerin solution into which 40 mg/ml recombinant human albumin was dissolved. The solution was applied to the left hand of an individual having chapped hands, leaving the right hand without treatment. The individual noticed a marked difference between the skin of the two hands. The skin of the treated hand was substantially softer than the right hand and healed rapidly despite repeated washing and no additional treatment. The solution had been applied sparingly but seemed to be rapidly absorbed by the skin. Once again, the compositions of the present invention were shown to be effective in achieving dermatological benefits with regard to healing and softening of skin.

What is claimed is:

1. A hypoallergenic cleansing composition for skin or hair consisting essentially of recombinant human serum albumin and a cleansing agent, wherein the human serum albumin is present in an amount sufficient to be absorbed into human skin or hair, wherein the human serum albumin is dissolved in a liquid soap and comprises 1 to 60 mg/ml of the human serum albumin in the liquid soap, and wherein the cleansing agent is present in an amount effective to cleanse skin or hair.

2. The cleansing composition according to claim 1 wherein the serum albumin is present at a concentration of 40 mg/ml.

3. The hypoallergenic cleansing composition for skin or hair according to claim 1 wherein the cleansing agent is in the form of a vehicle, carrier or excipient.

* * * * *

SEQUENCE LISTING

```
<160> NUMBER OF SEQ ID NOS: 5

<210> SEQ ID NO 1
<211> LENGTH: 5
<212> TYPE: PRT
<213> ORGANISM: Homo sapiens

<400> SEQUENCE: 1

Ala His Lys Ser Glu
1               5

<210> SEQ ID NO 2
<211> LENGTH: 4
```

```
<212> TYPE: PRT
<213> ORGANISM: Homo sapiens

<400> SEQUENCE: 2

His Lys Ser Glu
1

<210> SEQ ID NO 3
<211> LENGTH: 6
<212> TYPE: PRT
<213> ORGANISM: Homo sapiens

<400> SEQUENCE: 3

Asp Ala His Lys Ser Glu
1               5

<210> SEQ ID NO 4
<211> LENGTH: 6
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X can be any amino acid.

<400> SEQUENCE: 4

Asp Ala Xaa Lys Ser Glu
1               5

<210> SEQ ID NO 5
<211> LENGTH: 7
<212> TYPE: PRT
<213> ORGANISM: Homo sapiens

<400> SEQUENCE: 5

Glu Ala Glu Phe Asp Ala His
1               5
```